United States Patent
Zierke et al.

(10) Patent No.: US 8,492,558 B2
(45) Date of Patent: Jul. 23, 2013

(54) METHOD FOR PRODUCING 2-AMINOBIPHENYLENE

(75) Inventors: Thomas Zierke, Boehl-Iggelheim (DE); Volker Maywald, Ludwigshafen (DE); Sebastian Peer Smidt, Oftersheim (DE)

(73) Assignee: BASF SE, Ludwigshafen (DE)

( * ) Notice: Subject to any disclaimer, the term of this patent is extended or adjusted under 35 U.S.C. 154(b) by 108 days.

(21) Appl. No.: 13/201,562

(22) PCT Filed: Feb. 18, 2010

(86) PCT No.: PCT/EP2010/052033
§ 371 (c)(1),
(2), (4) Date: Aug. 15, 2011

(87) PCT Pub. No.: WO2010/094736
PCT Pub. Date: Aug. 26, 2010

(65) Prior Publication Data
US 2011/0301356 A1 Dec. 8, 2011

(30) Foreign Application Priority Data
Feb. 19, 2009 (EP) .................................... 09153239

(51) Int. Cl.
*C07D 231/14* (2006.01)
*C07C 211/59* (2006.01)

(52) U.S. Cl.
USPC ........................................ 548/374.1; 564/307

(58) Field of Classification Search
None
See application file for complete search history.

(56) References Cited

U.S. PATENT DOCUMENTS

| | | | |
|---|---|---|---|
| 5,330,995 | A | 7/1994 | Eicken et al. |
| 5,438,070 | A | 8/1995 | Eicken et al. |
| 5,998,450 | A | 12/1999 | Eicken et al. |
| 6,087,542 | A | 7/2000 | Eicken et al. |
| 8,008,232 | B2 | 8/2011 | Gewehr et al. |
| 2008/0108686 | A1 | 5/2008 | Gewehr et al. |
| 2009/0005597 | A1 | 1/2009 | Smidt et al. |
| 2011/0105760 | A1 | 5/2011 | Keil et al. |

FOREIGN PATENT DOCUMENTS

| | | |
|---|---|---|
| CA | 2 109 470 | 4/1994 |
| EP | 0 545 099 | 6/1993 |
| EP | 0 589 301 | 3/1994 |
| EP | 0 595 150 | 5/1994 |
| GB | 796 951 | 6/1958 |
| GB | 1 512 753 | 6/1978 |
| WO | WO 97 08148 | 3/1997 |
| WO | WO 97/33846 | 9/1997 |
| WO | WO 00 03743 | 1/2000 |
| WO | WO 2004/082677 | 9/2004 |
| WO | WO 2005/123690 | 12/2005 |
| WO | WO 2006/087343 | 8/2006 |
| WO | WO 2007/138089 | 12/2007 |
| WO | WO 2010/000856 | 1/2010 |

OTHER PUBLICATIONS

International Search Report prepared in International Application No. PCT/EP2010/052033, filed Feb. 18, 2010.
International Preliminary Report on Patentability from corresponding International Application No. PCT/EP2010/052033, filed Feb. 18, 2010.
Albert, J. et al., "Steric and electronic effects on E/Z composition of exocyclic cyclopalladated N-benzylideneamines", Journal of Organometallic Chemistry, (1997), pp. 131-137, vol. 545-546. Search Report.
Allan, Zdenek et al., "Aromatic Diazo Compounds XIV. The Phenylation of p-Phenylenediamine in the Nucleus and the Corresponding Reaction Mechanism", Chemicke Listy, 1953, pp. 52-60, vol. 47, Research Inst., Pardubice-Rybitvi, Czech. Search Report Translation Provided.
Allan, Zdenek et al, "Aromatic Diazo Compounds VIII Coupling with Benzidine", Chemicke Listy, 1952, pp. 485-486, vol. 46, Research Inst., Pardubice-Rybitvi, Czech. (XP 002504740) Search Report Abstract only.
Dai, C. et al., "The first general method for palladium-catalyzed negishi cross-coupling of aryl and vinyl chlorides: use of commercially available Pd(P(t-Bu)₃ )2 as a catalyst", Journal of Am. Chem. Soc., (2001), pp. 2719-2724, vol. 123. Search Report.
Hollingsworth, B.L. et al, "Some α ω-Di(phenanthridin-6-yl) alkanes", Journal of the Chemical Society, 1961, p. 3664-3667.
Jensen, A. et al., "Preparation of 2-arylted-1,4-phenylenediamines by palladium-catalyzed cross-coupling reactions", J. Org. Chem., (2002), pp. 122-128, vol. 653. Search Report.
Leardini, R. et al., "A new and convenient synthesis of phenanthridines", Synthesis, (1985), pp. 107-110, vol. 1985, No. 1. Search Report.
Li, G., "Highly active, air-stable palladium catalysts for the C-C and C-S bond-forming reactions of vinyl and aryl chlorides: use of commercially available [(t-Bu)₂P(OH)]₂PdCl₂,[(t-Bu)₂ P(OH)PdCl₂]2, and [[(t-Bu)2PO*H*OP(t_BU)₂ ]PDCl]₂ as catalysts", J. Org. Chem., (2002), pp. 3643-3650, vol. 67. Search Report.
Manolikakes, G. et al., "Palladium- and nickel-catalyzed cross-couplings of unsaturated halides bearing relatively acidic protons with organozinc reagents", J. Org. Chem., (2008), pp. 8422-8436, vol. 73. Search Report.
Niwa, H., "Studies on the syntheses of diphenyl derivatives (VI) on the amidines", Tohoku Yakka Daigaku Kenkyu Nempo, (1957), pp. 79-89, vol. 4. Search Report.

(Continued)

Primary Examiner — Kamal Saeed
(74) Attorney, Agent, or Firm — Brinks Hofer Gilson & Lione

(57) ABSTRACT

The present invention relates to a process for preparing 2-aminobiphenyls of the formula I

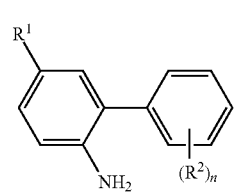

(I)

in which
n is 0, 1, 2 or 3,
$R^1$ is hydrogen, cyano or fluorine, and
each $R^2$ is independently selected from cyano, fluorine, $C_1$-$C_4$-alkyl, $C_1$-$C_4$-fluoroalkyl, $C_1$-$C_4$-alkoxy, $C_1$-$C_4$-fluoroalkoxy, $C_1$-$C_4$-alkylthio and $C_1$-$C_4$-fluoroalkylthio.
The invention also relates to a process for preparing pyrazole-carboxamides of such 2-aminobiphenyls.

12 Claims, No Drawings

OTHER PUBLICATIONS

Organ, M.G. et al., "A user friendly, all-purpose Pd-NHC (NHC=N-Heterocyclic Carbene) precatalyst for the Negishi reaction: A step towards a universal cross-coupling catalyst", Chem. Eur. J., (2006), pp. 4749-4755, vol. 12. Search Report.

Wetzel, Alexander et al., "Synthesis of amino-and hydroxybiphenyls by radical chain reaction of arenediazonium salts", Angewandte Chemie, International Edition, 2008, pp. 9130-9133, vol. 47 Search Report.

Xu, H. et al., "Palladium-phosphinous acid-catalyzed cross-coupling of aryl and acyl halides with aryl-, alkyl-, and vinylzinc reagents", J. Org. Chem. (2008), pp. 7638-7650, vol. 73. Search Report.

Campbell, J. et al., "Facile Palladium-Catalyzed Cross-Coupling of Monoorganozinc Halides with 3-Iodoanthranilonitriles", Synthetic Communications, (1989), pp. 2265-2272, vol. 19.

Jeong, N. et al., "A Facile Preparation of the Fluoroaryl Zinc Halides: an Application to the Synthesis of Diflunisal", Bull. Korean Chem. Soc. (2000), pp. 165-166, vol. 21, No. 2.

Negishi, E. et al., "Selective Carbon-Carbon Bond Formation via Transition Metal Catalysis. 3.[1] A Highly Selective Synthesis of Unsymmetrical Biaryls and Diarylmethanes by the Nickel- or Palladium- Catalyzed Reaction of Aryl- and Benzylzinc Derivatives with Aryl Halides", J. Org. Chem., (1977), pp. 1821-1823, vol. 42, No. 10.

METHOD FOR PRODUCING 2-AMINOBIPHENYLENE

This application is a National Stage application of International Application No. PCT/EP2010/052033, filed Feb. 18, 2010, the entire contents of which is hereby incorporated herein by reference. This application also claims priority under 35 U.S.C. §119 to European Patent Application No. 09153239.0 filed Feb. 19, 2009, the entire contents of which is hereby incorporated herein by reference.

The present invention relates to a process for preparing 2-aminobiphenyls of the formula I

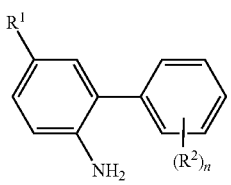

(I)

in which
n is 0, 1, 2 or 3,
$R^1$ is hydrogen, cyano or fluorine, and
each $R^2$ is independently selected from cyano, fluorine, $C_1$-$C_4$-alkyl, $C_1$-$C_4$-fluoroalkyl, $C_1$-$C_4$-alkoxy, $C_1$-$C_4$-fluoroalkoxy, $C_1$-$C_4$-alkylthio and $C_1$-$C_4$-fluoroalkylthio.

The invention also relates to a process for preparing pyrazolecarboxamides of such 2-aminobiphenyls.

2-Aminobiphenyls of the formula I are important precursors for aryl- and hetarylcarboxamides, which find use especially as fungicides. Such fungicides are disclosed, for example, in WO 2006/087343, WO 2005/123690, EP 0589301 and EP 0545099. Prominent representatives thereof include boscalid (2-chloro-N-(4'-chlorobiphenyl-2-yl)pyridine-3-carboxamide) and bixafen (N-(3',4'-dichloro-5-fluorobiphenyl-2-yl)-3-(difluoromethyl)-1-methylpyrazole-4-carboxamide).

For preparation of substituted 2-aminobiphenyls of the formula I, a process described in WO 97/33846 has been found to be useful, which is based on the coupling of 2-nitrochlorobenzene with halogen-substituted aromatic boronic acids to the correspondingly substituted 2-nitrobiphenyls, which are subsequently reduced to 2-aminobiphenyls. However, this is a multistage synthetic route, which is consequently time-consuming and costly. For instance, it requires both the provision of the boronic acids, which are typically prepared in three stages, proceeding from haloaromatics via Grignard compounds, boronic esters and subsequent hydrolysis, and the final hydrogenation of the nitro function.

Palladium-catalyzed cross-couplings of haloaromatics with zinc organyls, known as Negishi couplings, have been known for some time (E. Negishi et al., J. Org. Chem. 1977, 42; E. Negishi in "Metal-catalyzed Cross-Coupling Reactions; F. Diederich, P. J. Stang (eds.) Wiley-VCH, Weinheim, 1998, p. 1821). The reaction of the relatively unreactive chloroaromatics in the manner of a Negishi coupling has been reported in individual cases (C. Dai, G. C. Fu, J. Am. Chem. Soc. 2001, 123, 2719).

For the preparation of 2-aminobiphenyls, the Negishi coupling has been used to date only proceeding from the particularly reactive iodoaniline derivatives. For instance, reactions of 2- or 3-iodoaniline and of 3-iodoanthranilonitrile with arylzinc iodides are known (N. Jeong et al., Bull. Korean Chem. Soc. 2000, 21, 165; J. B. Campbell et al., Synth. Comm. 1989, 19, 2265). In order to achieve good coupling yields, it was necessary, however, to use large excesses of zinc organyl and 5 to 6 mol % of palladium catalyst, which greatly limits the economic significance of these processes for many applications.

Knochel et al., J. Org. Chem. 2008, 73, 8422, likewise describe the use of arylzinc iodides for syntheses of aminobiphenyls by means of palladium-catalyzed cross-couplings. The aryl halide components that they use for this purpose are aryl bromides, since they found aryl chlorides to be unsuitable. In addition, great excesses of zinc organyl were again required for the syntheses described.

It was an object of the present invention to provide processes, performable in a simple manner and on the industrial scale, for preparing substituted 2-aminobiphenyls and for preparing pyrazolecarboxamides derived therefrom. These processes should additionally be inexpensive and be based on selective reactions. Thus, a route to substituted 2-aminobiphenyls proceeding from less reactive 2-chloroanilines which, however, are more readily available and/or less expensive compared to the corresponding 2-bromoanilines, is also to be found.

The object is achieved by the processes described in detail hereinafter.

The present invention provides a process for preparing the substituted 2-aminobiphenyls of the formula I defined at the outset, comprising the following steps:
(i) reacting an aniline compound of the formula II with a zinc organyl compound of the formula III

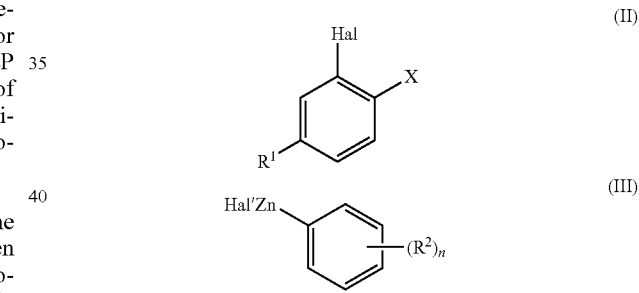

in which
Hal and Hal' are each independently bromine or chlorine,
n, $R^1$ and $R^2$ are each as defined above, and
X is $NH_2$ or an $X^1$ or $X^2$ radical
$X^1$:

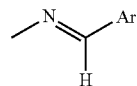

$X^2$:

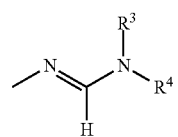

in which
Ar is phenyl which optionally bears 1, 2 or 3 substituents which are selected from $C_1$-$C_4$-alkyl and $C_1$-$C_4$-alkoxy, and $R^3$ and $R^4$ are each independently $C_1$-$C_6$-alkyl, in the presence of a palladium catalyst comprising palladium and one or more complex ligands, and, when X in formula II is an $X^1$ or $X^2$ radical, (ii) converting the product obtained in step (i) to a 2-aminobiphenyl of the formula I.

The process according to the invention is associated with a series of advantages. For instance, the process according to the invention enables preparation of 2-aminobiphenyls of the formula I inexpensively, in good to very good yields and with high selectivities. More particularly, it allows the preparation of 2-aminobiphenyls from the less reactive chloroaniline compounds II (Hal=Cl).

In the context of the present invention, the terms used generically are each defined as follows:

The prefix $C_x$-$C_y$ refers in the particular case to the number of possible carbon atoms.

The term "halogen" denotes in each case fluorine, bromine, chlorine or iodine, especially fluorine, chlorine or bromine.

The term "$C_1$-$C_4$-alkyl" denotes a linear or branched alkyl radical comprising 1 to 4 carbon atoms, such as methyl, ethyl, propyl, 1-methylethyl(isopropyl), butyl, 1-methylpropyl (sec-butyl), 2-methylpropyl(isobutyl) or 1,1-dimethylethyl (tert-butyl).

The term "$C_1$-$C_6$-alkyl" denotes a linear or branched alkyl radical comprising 1 to 6 carbon atoms. Examples are, in addition to the radicals mentioned for $C_1$-$C_4$-alkyl, pentyl, hexyl, 2,2-dimethylpropyl, 2-methylbutyl, 3-ethylbutyl, 4-methylpentyl and positional isomers thereof.

The term "$C_1$-$C_4$-fluoroalkyl", as used herein and in the fluoroalkyl units of $C_1$-$C_4$-fluoroalkoxy and $C_1$-$C_4$-fluoroalkylthio, describes straight-chain or branched alkyl groups having 1 to 4 carbon atoms, where some or all of the hydrogen atoms of these groups are replaced by fluorine atoms. Examples thereof are fluoromethyl, difluoromethyl, trifluoromethyl, 1-fluoroethyl, 2-fluoroethyl, 2,2-difluoroethyl, 2,2,2-trifluoroethyl, pentafluoroethyl, 3,3,3-trifluoroprop-1-yl, 1,1,1-trifluoroprop-2-yl, heptafluoroisopropyl, 1-fluorobutyl, 2-fluorobutyl, 3-fluorobutyl, 4-fluorobutyl, 4,4,4-trifluorobutyl, fluoro-tert-butyl and the like.

The term "halomethyl" describes methyl groups, some or all of whose hydrogen atoms are replaced by halogen atoms. Examples thereof are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, dibromomethyl, tribromomethyl, chlorobromomethyl, dichlorobromomethyl, chlorodibromomethyl and the like.

The term "$C_1$-$C_4$-alkoxy" denotes straight-chain or branched saturated alkyl groups which comprise 1 to 4 carbon atoms and are bonded via an oxygen atom. Examples of $C_1$-$C_4$-alkoxy are methoxy, ethoxy, n-propoxy, 1-methylethoxy(isopropoxy), n-butoxy, 1-methylpropoxy(sec-butoxy), 2-methylpropoxy(isobutoxy) and 1,1-dimethylethoxy (tert-butoxy).

The term "$C_1$-$C_4$-fluoroalkoxy" describes straight-chain or branched saturated fluoroalkyl groups which comprise 1 to 4 carbon atoms and are bonded via an oxygen atom. Examples thereof are fluoromethoxy, difluoromethoxy, trifluoromethoxy, 1-fluoroethoxy, 2-fluoroethoxy, 2,2-difluoroethoxy, 2,2,2-trifluoroethoxy, 1,1,2,2-tetrafluoroethoxy, pentafluoroethoxy, 3,3,3-trifluoroprop-1-oxy, 1,1,1-trifluoroprop-2-oxy, 1-fluorobutoxy, 2-fluorobutoxy, 3-fluorobutoxy, 4-fluorobutoxy and the like.

The term "$C_1$-$C_4$-alkylthio" denotes straight-chain or branched saturated alkyl groups which comprise 1 to 4 carbon atoms and are bonded via a sulfur atom. Examples of $C_1$-$C_4$-alkylthio are methylthio, ethylthio, n-propylthio, 1-methylethylthio(isopropylthio), n-butylthio, 1-methylpropylthio (sec-butylthio), 2-methylpropylthio(isobutylthio) and 1,1-dimethylethylthio(tert-butylthio).

The term "$C_1$-$C_4$-fluoroalkylthio" describes straight-chain or branched saturated fluoroalkyl groups which comprise 1 to 4 carbon atoms and are bonded via a sulfur atom. Examples thereof are fluoromethylthio, difluoromethylthio, trifluoromethylthio, 1-fluoroethylthio, 2-fluoroethylthio, 2,2-difluoroethylthio, 2,2,2-trifluoroethylthio, 1,1,2,2-tetrafluoroethylthio, pentafluoroethylthio, 3,3,3-trifluoroprop-1-ylthio, 1,1,1-trifluoroprop-2-ylthio, 1-fluorobutylthio, 2-fluorobutylthio, 3-fluorobutylthio, 4-fluorobutylthio and the like.

The term "aryl" denotes carbocyclic aromatic radicals having 6 to 14 carbon atoms. Examples thereof comprise phenyl, naphthyl, fluorenyl, azulenyl, anthracenyl and phenanthrenyl. Aryl is preferably phenyl or naphthyl and especially phenyl.

The term "hetaryl" denotes aromatic radicals having 1 to 4 heteroatoms which are selected from O, N and S. Examples thereof are 5- and 6-membered hetaryl radicals having 1, 2, 3 or 4 heteroatoms selected from O, S and N, such as pyrrolyl, furanyl, thienyl, pyrazolyl, imidazolyl, oxazolyl, isoxazolyl, thiazolyl, isothiazolyl, triazolyl, tetrazolyl, pyridyl, pyrazinyl, pyridazinyl, pyrimidyl and triazinyl.

In the compounds of the formulae I, Ia, Ib, III and IV, n is preferably 1, 2 or 3 and especially preferably 3. When n is 1, $R^2$ is preferably in the para or meta position to the biphenyl or zinc bond, and, when n is 2 or 3, $R^2$ is preferably in the para and meta positions to the biphenyl or zinc bond.

In the compounds of the formulae I, Ia, Ib, II and IV, $R^1$ is preferably hydrogen or fluorine and especially preferably hydrogen.

In the compounds of the formulae I, Ia, Ib, III and IV, $R^2$ is preferably fluorine, $C_1$-$C_4$-alkyl or $C_1$-$C_4$-fluoroalkyl and especially preferably fluorine.

In the compounds of the formula III, Hal' is preferably chlorine.

In the compounds of the formula II, X is preferably $X^1$ or $X^2$, where, in the definitions of $X^1$ and $X^2$ and in the compounds of the formulae (Ia) and (Ib), the substituent Ar is preferably unsubstituted phenyl and the substituents $R^3$ and $R^4$ are preferably each methyl.

In the compounds of the formulae IV and V, $R^5$ is preferably methyl or fluoromethyl and especially preferably methyl, difluoromethyl or trifluoromethyl.

In a first embodiment of the invention, the variable Hal in the compounds of the formulae II, IIa and IIb is bromine.

In a second, preferred embodiment of the invention, the variable Hal in the compounds of the formulae II, IIa and IIb is chlorine.

The inventive conversions described hereinafter are performed in reaction vessels customary for such reactions, the reaction being configurable in a continuous, semicontinuous or batchwise manner. In general, the particular reactions will be performed under atmospheric pressure. The reactions may, however, also be performed under reduced or elevated pressure.

The conversion in step (i) of the process according to the invention for preparing substituted 2-aminobiphenyls I is a Negishi cross-coupling. The reaction is effected by contacting the starting compounds, i.e. an aniline compound II and a zinc organyl compound III, and also a palladium catalyst, preferably in a solvent, under suitable reaction conditions.

In general, step (i) is performed under temperature control. The Negishi coupling is effected typically in a closed or unclosed reaction vessel with stirring and heating apparatus.

The reactants can in principle be contacted with one another in any desired sequence. For example, the aniline compound II, optionally dissolved in a solvent or in dispersed form, can be initially charged and admixed with the zinc organyl III or, conversely, the zinc organyl III, optionally dissolved in a solvent or in dispersed form, can be initially charged and admixed with the aniline compound. Alternatively, the two reactants can also be added simultaneously to the reaction vessel. The palladium catalyst can be added before or after the addition of one of the reactants or else together with one of the reactants, either in a solvent or in bulk.

It has been found to be appropriate to initially charge the zinc organyl III, preferably in a solvent, and to add the palladium catalyst, or a palladium source and one or more complexing ligands from which the active catalyst is formed, and the aniline compound II.

Suitable solvents depend in the individual case on the selection of the particular reactants and reaction conditions. It has generally been found to be advantageous, as the solvent for the conversion of the compounds (II) and (III), to use an aprotic organic solvent. Useful aprotic organic solvents here include, for example, aliphatic $C_3$-$C_6$ ethers, such as dimethoxyethane, diethylene glycol dimethyl ether, dipropyl ether, methyl isobutyl ether, tert-butyl methyl ether and tert-butyl ethyl ether, aliphatic hydrocarbons, such as pentane, hexane, heptane and octane, and also petroleum ether, cycloaliphatic hydrocarbons, such as cyclopentane and cyclohexane, alicyclic $C_3$-$C_6$ ethers, such as tetrahydrofuran, tetrahydropyran, 2-methyltetrahydrofuran, 3-methyltetrahydrofuran and dioxane, aromatic hydrocarbons, such as benzene, toluene, the xylenes and mesitylene, short-chain ketones, such as acetone, ethyl methyl ketone and isobutyl methyl ketone, amides such as dimethylformamide, dimethylacetamide and N-methylpyrrolidone, dimethyl sulfoxide, acetonitrile, or mixtures of these solvents with one another.

The solvent for the conversion in step (i) preferably comprises at least one ether, especially an aliphatic or alicyclic $C_3$-$C_6$ ether, or a mixture of at least one of the aforementioned ethers with at least one amide, especially N-methylpyrrolidone. The aforementioned solvents preferably make up at least 70% by weight, especially at least 90% by weight, of the total amount of solvent. However, it is possible to dilute the aforementioned solvents with hydrocarbons, especially aromatic hydrocarbons, the proportion of hydrocarbons making up preferably not more than 30% by weight, especially not more than 10% by weight, of the total amount of solvent. Among the aforementioned mixtures, mixtures of tetrahydrofuran with N-methylpyrrolidone are particularly preferred, in which case the zinc organyl III is preferably initially charged in THF, then the palladium catalyst and N-methylpyrrolidone, either together or in succession, are added and, thereafter, the aniline compound II is added. In the case of conversion of an aniline compound II in which X is $NH_2$, the weight ratio of tetrahydrofuran to N-methylpyrrolidone is preferably in the range from 5:1 to 1:7 and more preferably in the range from 3:1 to 1:4. In the case of conversion of an aniline compound II in which X is $X^1$ or $X^2$, the weight ratio of tetrahydrofuran to N-methyl-pyrrolidone is preferably in the range from 15:1 to 1:1 and more preferably in the range from 10:1 to 3:1.

The total amount of the solvent used in step (i) of the process according to the invention is typically in the range from 100 to 3000 g and preferably in the range from 150 to 2000 g, based on 1 mol of the zinc organyl III.

Preference is given to using solvents which are essentially anhydrous, i.e. have a water content of less than 1000 ppm and especially not more than 100 ppm.

In a preferred embodiment of the invention, in step (i), the aniline compound of the formula II, if X is $NH_2$, is used in an amount of 0.1 to 1 mol, more preferably of 0.3 to 0.9 mol and especially of 0.5 to 0.8 mol, based in each case on 1 mol of the zinc organyl of the formula III. If, in contrast, X is $X^1$ or $X^2$, the aniline compound II is preferably used in an amount of 0.5 to 1.5 mol, more preferably of 0.7 to 1.3 mol and especially of 0.9 to 1.1 mol, based in each case on 1 mol of the zinc organyl III.

As already stated, in a preferred embodiment, the zinc organyl III, for the conversion in step (i), is initially charged dissolved in a solvent or in dispersed form. For this purpose, the zinc organyl can either be used directly or formed in situ. The in situ formation is typically effected analogously to known procedures, as described, for example, by Fu et al., J. Am. Chem. Soc. 2001, 123, 2721, by trans-metalation of an organometallic precursor of the zinc organyl III with an approximately equimolar amount of a zinc salt, preferably zinc chloride or zinc bromide and especially zinc chloride. The organometallic precursors used here are preferably the corresponding organolithium compounds or the corresponding organomagnesium Grignard compounds. The structure of these preferred precursor compounds can be derived from the formula III, by replacing the "Hal'Zn" substituent with "Li" or "Hal"Mg", where Hal" is preferably chlorine or bromine. The reaction for in situ formation is preferably undertaken in a solvent, which is generally one of the aforementioned aprotic solvents, more preferably ether and especially THF. Typically, a precursor compound is reacted with a zinc salt at a temperature of generally 10 to 50° C. and preferably of 15 to 35° C. over a period of 1 to 60 minutes and preferably of 5 to 30 minutes. The zinc organyl III thus obtained, typically present in a solvent, is reacted in step (i).

It is suspected that the mechanism of the reaction in step (i) corresponds to the mechanism proposed for the Negishi cross-coupling. According to this, in the first step, the oxidative addition, the insertion of palladium(0) from the catalyst into the R-Hal bond of the aniline compound II forms an organylpalladium(II) complex. In the second step, the organyl radical of the organozinc compound III is transferred to the palladium(II). In the next step, the trans/cis isomerization, the two organyl ligands newly inserted into the palladium complex rearrange such that they are in the cis position relative to one another. In the last step, the reductive elimination, the two radicals are coupled to one another by C—C bond formation with reduction of palladium(II) to palladium(0).

As explained above, in step (i), an aniline compound II either with a free amino function (X is $NH_2$) or, in a preferred embodiment of the invention, with a protected amino function, where X is either $X^1$ or $X^2$, is used. The latter is the imine derivative IIa or the amidine derivative IIb of the aniline compound II with a free $NH_2$ group:

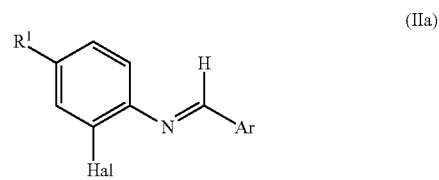

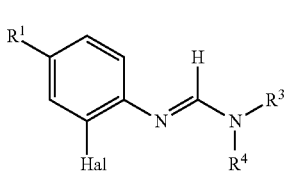

(IIb)

where $R^1$, $R^3$, $R^4$, Ar and Hal are each as defined above.

In the process according to the invention for preparing compounds I, the use of the aniline compounds II with a free amino function has the advantage over the protected compounds IIa or IIb that two synthesis steps fewer are required. One is the conversion of an aniline compound II with a free amino function to an imine derivative of the formula IIa or to an amidine derivative of the formula IIb, and the other is the release of the amino group in step (ii) of the process according to the invention. On the other hand, the use of the protected compounds IIa or IIb has surprising advantages over the use of the free amine II (X=NH$_2$). For instance, the reactions of the free amine in step (i), especially at relatively high temperatures, which might be required owing to a relatively low reactivity of the reactants used or of the palladium catalyst used, lead under some circumstances to lower yields and the increased occurrence of undesired by-products. Reactions of the compounds IIa or IIb in step (i) succeed, in contrast, generally in high yields without significant formation of by-products. It is suspected that the higher bulk of the protected amino function in the ortho position to the halogen-carbon bond, into which the catalytically active palladium is first inserted oxidatively, accelerates the exit from the ligand sphere of the palladium in the last step of the catalytic process.

Zinc organyl compounds of the formula III and the imine- or amidine-derivatized aniline compounds of the formulae IIa and IIb are common knowledge and can be prepared by customary processes. For instance, the zinc organyls III are obtainable as described above by trans-metalation, preferably from the corresponding organolithium and organomagnesium compounds. The imines IIa can advantageously be obtained by reacting the corresponding aniline compound II with optionally substituted benzaldehyde. To prepare an amidine IIb, the corresponding aniline compound II is preferably reacted with an activated derivative of the particular dialkylformamide, especially an acetal of the dialkylformamide.

Suitable palladium catalysts for the reaction of the compounds II with compounds III in step (i) of the process according to the invention are palladium compounds in which palladium has an oxidation state of 0 or 2.

Examples of palladium compounds which have an oxidation state of 0 are palladium(0)-ligand complexes, such as tetrakis(triphenylphosphine)palladium(0), tetrakis(diphenylmethylphosphine)palladium(0) or bis(DIPHOS)palladium (0), or metallic palladium which is supported if appropriate. Metallic palladium is preferably applied to an inert support, such as activated carbon, aluminum oxide, barium sulfate, barium carbonate or calcium carbonate. The reaction in the presence of metallic palladium is effected preferably in the presence of suitable complex ligands.

Examples of palladium compounds which have an oxidation state of 2 are palladium(II)-ligand complexes, such as palladium(II) acetylacetonate or compounds of the formula PdX$_2$L$_2$ in which X is halogen and L is especially one of the ligands mentioned below, and also palladium(II) salts, for example palladium acetate or palladium chloride.

The palladium catalyst can be used in the form of a finished palladium complex or as a palladium compound which, under the reaction conditions, as a precatalyst, together with suitable ligands, forms the catalytically active compound.

In the case of use of palladium(II) salts as the precatalyst, the reaction is effected preferably in the presence of suitable complex ligands, especially of the complex ligands specified hereinafter. Useful palladium(II) salts for this purpose are, for example, palladium(II) chloride, bisacetonitrilepalladium(II) chloride and palladium(II)acetate. Preference is given to using palladium(II) chloride for this purpose.

Suitable complex ligands for the conversion in step (i) of the process according to the invention are, for example, mono- or bidentate phosphines of the formulae VI and VII shown below

(VI)

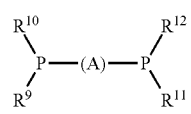

(VII)

in which $R^6$ to $R^{12}$ are each independently C$_1$-C$_8$-alkyl, C$_5$-C$_8$-cycloalkyl, adamantyl, aryl-C$_1$-C$_2$-alkyl, ferrocenyl or aryl which is optionally substituted by C$_1$-C$_4$-alkyl, C$_1$-C$_4$-alkoxy, fluorine or chlorine, and A is ferrocenediyl or a linear C$_2$-C$_5$-alkanediyl which is optionally substituted by C$_1$-C$_8$-alkyl or C$_3$-C$_6$-cycloalkyl and is optionally part of one or two mono- or bicyclic rings which are unsubstituted or substituted.

More particularly, A in the compound of the formula VII is C$_2$-C$_4$-alkylene, C$_0$-C$_1$-alkyleneferrocenyl, 1,1'-biphenyl-2,2'-diyl or 1,1'-binaphthyl-2,2'-diyl, where the latter four groups may optionally be substituted by C$_1$-C$_8$-alkyl or C$_1$-C$_4$-alkoxy, and where C$_2$-C$_4$-alkylene may additionally have one or more substituents selected from C$_3$-C$_7$-cycloalkyl, aryl and benzyl. In this connection, 1 to 4 carbon atoms of the C$_2$-C$_4$-alkylene may be part of a C$_3$-C$_7$-cycloalkyl ring. Aryl here is naphthyl or optionally substituted phenyl. Aryl is preferably phenyl or tolyl, more preferably phenyl. C$_0$-C$_1$-Alkyleneferrocenyl is especially ferrocenediyl, where one of the two phosphorus atoms in each case is bonded to each cyclopentadiene of the ferrocene, or methyleneferrocenyl, where one of the phosphorus atoms is bonded via the methylene group to a cyclopentadiene, the second phosphorus atom is bonded to the same cyclopentadiene, and the methylene group may optionally have 1 or 2 further substituents selected from C$_1$-C$_4$-alkyl.

Monodentate complex ligands of the formula VI preferred for the inventive conversions are those in which R$^6$, R$^7$ and R$^8$ are each optionally substituted phenyl, for example triphenylphosphine (TPP), and those in which R$^6$, R$^7$ and R$^8$ are each C$_1$-C$_6$-alkyl, C$_5$-C$_8$-cycloalkyl or adamantyl, for example di-1-adamantyl-n-butylphosphine, tri-tert-butylphosphine (TtBP), methyldi-tert-butylphosphine, tricyclohexylphosphine and 2-(dicyclohexylphosphino)biphenyl. In addition, it is also possible to use phosphites, for example tris(2,4-di-tert-butylphenyl) phosphite (cf. A. Zapf et al., Chem. Eur. J. 2000, 6, 1830).

In a preferred embodiment of the invention, the complex ligand used in the reaction in step (i) of the process according to the invention comprises a bidentate complex ligand of the formula VII. Among the bidentate ligands of the formula VII, especially preferred ligands are those which correspond to the formula VIII:

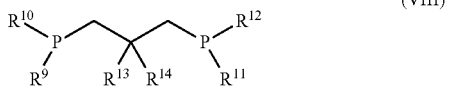

(VIII)

in which $R^9$ to $R^{12}$ are each as defined above and are preferably each independently phenyl which optionally bears one to three substituents selected from methyl, methoxy, fluorine and chlorine. $R^{13}$ and $R^{14}$ are each independently hydrogen, $C_1$-$C_8$-alkyl or $C_3$-$C_6$-cycloalkyl, or $R^{13}$ and $R^{14}$ form, together with the carbon atom to which they are bonded, a 3- to 8-membered ring which is optionally substituted by $C_1$-$C_6$-alkyl. $R^{13}$ and $R^{14}$ are preferably each independently selected from methyl, ethyl, 1-methylethyl, n-butyl, 1-methylpropyl, 2-methylpropyl, pentyl, 1-methylbutyl, 2-methylbutyl, 3-methylbutyl, hexyl, 1-methylpentyl, 2-methylpentyl, 3-methylpentyl, 4-methylpentyl, cyclopropyl, cyclobutyl, cyclopentyl or cyclohexyl. Examples of preferred compounds of the formula (VIII) are 1,3-bis(diphenylphosphinyl)-2-methylpropane, 1,3-bis(diphenylphosphinyl)-2,2-dimethylpropane, 1,3-bis(diphenylphosphinyl)-2-methyl-2-ethylpropane, 1,3-bis(diphenylphosphinyl)-2,2-diethylpropane, 1,3-bis(diphenylphosphinyl)-2-methyl-2-propylpropane, 1,3-bis(diphenylphosphinyl)-2-ethyl-2-propylpropane, 1,3-bis(diphenylphosphinyl)-2,2-dipropylpropane, 1,3-bis(diphenylphosphinyl)-2-methyl-2-butylpropane, 1,3-bis(diphenylphosphinyl)-2-ethyl-2-butylpropane, 1,3-bis(diphenylphosphinyl)-2-propyl-2-butylpropane, 1,3-bis(diphenylphosphinyl)-2,2-dibutylpropane, 1,3-bis(diphenylphosphinyl)-2-methyl-2-cyclopropylpropane, 1,3-bis(diphenylphosphinyl)-2-methyl-2-cyclobutylpropane, 1,3-bis(diphenylphosphinyl)-2-methyl-2-cyclopentylpropane, 1,3-bis(diphenylphosphinyl)-2-methyl-2-cyclohexylpropane. Examples of particularly preferred compounds of the formula (VIII) are 1,3-bis(diphenylphosphinyl)-2,2-dimethylpropane and 1,3-bis(diphenylphosphinyl)-2-ethyl-2-butylpropane.

In a further preferred embodiment of the invention, the ligands used as complex ligands in the conversion in step (i) of the process according to the invention comprise at least one N-heterocyclic carbene, known as NHC ligands. These are, more particularly, reactive complex ligands, which are described, for example, in G. A. Grasa et al., Organometallics 2002, 21, 2866. NHC ligands can be obtained in situ from imidazolium salts, for example 1,3-bis(2,6-diisopropylphenyl)-4,5-H2-imidazolium chloride, with bases, and be converted to suitable catalysts in the presence of palladium(0) compounds, especially of the tris(dibenzylideneacetone)dipalladium(0) or bis-(dibenzylideneacetone)palladium(0) type, or palladium(II) salts such as palladium(II)acetate. However, it is also possible to prepare (NHC)palladium(II) complex salts, especially (1,3-bis(2,6-diisopropylphenyl)imidazol-2-ylidene)(3-chloropyridyl)-palladium(II)dichloride, beforehand and to isolate them, and then to use them as preformed catalysts in the inventive cross-couplings (cf. S. P. Nolan, Org. Lett. 2005, 7, 1829 and M. G. Organ, Chem. Eur. J. 2006, 12, 4749).

For the inventive reactions, the NHC ligands used are preferably sterically hindered imidazol-2-ylidene compounds, especially those of the formula IX which bear bulky $R^{15}$ and $R^{16}$ substituents in positions 1 and 3 of the imidazole ring. Preferably, $R^{15}$ and $R^{16}$ here are each independently aryl or hetaryl, each of which is unsubstituted or bears 1, 2, 3 or 4 substituents, where the substituents are preferably selected from $C_1$-$C_8$-alkyl and $C_3$-$C_7$-cycloalkyl. Particularly preferred $R^{15}$ and $R^{16}$ substituents are phenyl radicals which bear, in positions 2 and 6, preferably branched $C_1$-$C_6$-alkyl radicals.

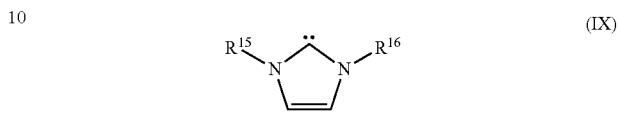

(IX)

In a further preferred embodiment of the invention, for the conversion in step (i) of the process according to the invention, a palladium complex is used, which bears, as complex ligands, at least one of the aforementioned NHC ligands and optionally at least one further coligand. Such coligands are, for example, selected from hetaryl with at least one nitrogen atom in the ring, especially pyridyl which is unsubstituted or bears 1, 2 or 3 substituents selected from halogen, $C_1$-$C_6$-alkyl and $C_1$-$C_8$-alkoxy. A specific example of such a coligand is 3-chloropyridyl.

In a particularly preferred embodiment of the invention, for the conversion in step (i) of the process according to the invention, complex ligands are used, which are selected from tri-tert-butylphosphine, methyldi-tert-butylphosphine, 1,3-bis(diphenylphosphinyl)-2,2-dimethylpropane, 1,3-bis(diphenylphosphinyl)-2-ethyl-2-butylpropane and 1,3-bis-(2,6-diisopropylphenyl)imidazol-2-ylidene.

When a palladium compound is used in the process according to the invention as a precatalyst together with suitable ligands, generally 0.5 to 5 molar equivalents of the aforementioned complex ligands are combined with one equivalent of a palladium(II) salt or of a palladium(0) compound. Particular preference is given to the use of one to three molar equivalents of complex ligand, based on the palladium compound.

The palladium catalyst is used in the process according to the invention preferably in an amount of 0.001 to 5.0 mol %, preferably of 0.01 to 1.0 mol %, and especially of 0.1 to 0.5 mol %, based on the amount of the zinc organyl compound III used.

The reaction temperature of step (i) is determined by several factors, for example the reactivity of the reactants used and the type of the palladium catalyst selected, and can be determined by the person skilled in the art in the individual case, for example by simple preliminary tests. In general, the conversion in step (i) of the process according to the invention is performed at a temperature in the range from 0 to 200° C., preferably in the range from 10 to 130° C., especially in the range from 25 to 130° C. and more preferably in the range from 30 to 65° C. Depending on the solvent used, on the reaction temperature and on whether the reaction vessel possesses a vent, a pressure of generally 1 to 6 bar and preferably of 1 to 4 bar is established during the reaction.

The reaction product obtained from the conversion in step (i) of the process according to the invention is, if an aniline compound II in which X is $NH_2$ is used, a 2-aminobiphenyl of the formula I. The workup of the resulting reaction mixture is effected generally with an aqueous acid, i.e. the reaction mixture is contacted with an aqueous solution of an acid. Preference is given to using aqueous mineral acids, especially hydrochloric acid, in concentrations of generally 1 to 25% by weight and preferably of 5 to 15% by weight. Optionally, before or after the addition of the aqueous acid, the palladium catalyst obtained in solid form is removed, for example by filtration. The 2-aminobiphenyl of the formula I can generally be isolated from the aqueous reaction mixture thus obtained by extraction with an organic solvent and subsequent removal of the organic solvent. In general, it is advantageous, before the performance of the extraction, to adjust the pH of the acidified aqueous reaction mixture with a base, preferably an aqueous sodium hydroxide solution, to a value in the basic range, preferably in the range from 9 to 13. The 2-aminobiphenyl I thus isolated can subsequently be retained for uses or be sent directly to a use, for example in a further reaction step, or be purified further beforehand. For further purification, it is possible to use one or more methods known to those skilled in the art, for example recrystallization, distillation, sublimation, zone melting, melt crystallization or chromatography.

If, in contrast, an aniline compound II in which X is $X^1$ or $X^2$ is used in step (i) of the process according to the invention, a biphenyl compound Ia or Ib is obtained as the reaction product, which can be used either with or without preceding workup in step (ii) of the process according to the invention. The workup is effected typically by aqueous or nonaqueous means. For aqueous workup, the reaction mixture is generally contacted with an optionally acidified aqueous solution. The acidified aqueous solution is preferably a dilute aqueous solution of a mineral acid, especially hydrochloric acid, with a concentration of 0.001 to 5% by weight and especially of 0.1 to 3% by weight. Optionally, before or after the addition of the aqueous solution, the palladium catalyst obtained in solid form is removed, for example by filtration. From the aqueous reaction mixture thus obtained, the biphenyl compound of the formula Ia or Ib can generally by isolated by extraction with an organic solvent and subsequent removal of the organic solvent. For nonaqueous workup, the reaction mixture, after it has been treated, optionally, with activated carbon for example, is generally filtered, for example through kieselguhr, and the product is isolated by removing the solvent from the filtrate. The biphenyl compound Ia or Ib thus obtained after an aqueous or nonaqueous workup can be used directly in step (ii) of the process according to the invention or sent to other uses. Alternatively, it can be retained for a further use or first purified further using methods known to those skilled in the art.

The compounds Ia and Ib are novel and likewise form part of the subject matter of the present invention:

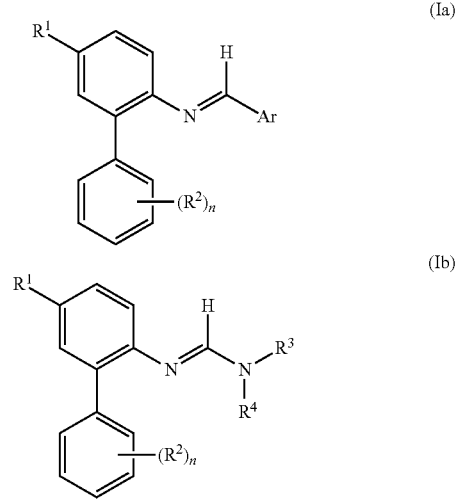

where n, $R^1$, $R^2$, $R^3$, $R^4$ and Ar are each as defined above.

In preferred compounds of the formula Ia, n is 1, 2 or 3, and each $R^2$ is independently cyano, fluorine, $C_1$-$C_4$-alkyl, $C_1$-$C_4$-fluoroalkyl, $C_1$-$C_4$-fluoroalkoxy, $C_1$-$C_4$-alkylthio or $C_1$-$C_4$-fluoroalkylthio, especially fluorine, $C_1$-$C_4$-alkyl or $C_1$-$C_4$-fluoroalkyl. In preferred compounds of the formula Ib, n is 1, 2 or 3, and each $R^2$ is independently cyano, fluorine, $C_1$-$C_4$-alkyl, $C_1$-$C_4$-fluoroalkyl, $C_1$-$C_4$-alkoxy, $C_1$-$C_4$-fluoroalkoxy, $C_1$-$C_4$-alkythio or $C_1$-$C_4$-fluoroalkylthio, especially fluorine, $C_1$-$C_4$-alkyl or $C_1$-$C_4$-fluoroalkyl. In particularly preferred compounds of the formula Ia or Ib, n is 1, 2 or 3 and each $R^2$ is fluorine. $R^1$ is especially hydrogen or fluorine. Ar is especially phenyl. $R^3$ and $R^4$ are especially each methyl or ethyl. A very particularly preferred compound of the formula Ia is 2-phenylmethylideneamino(3',4',5'-trifluoro)biphenyl and a very particularly preferred compound of the formula Ib is N,N-dimethyl-N'-(3',4',5'-trifluorobiphenyl-2-yl)-formamidine.

In step (ii) of the process according to the invention for preparing substituted 2-aminobiphenyls I, the reaction product obtained from step (i) is generally converted under hydrolytic conditions, in order to convert imine or amidine groups present to amino groups. Typically, step (ii) is performed under temperature control and, in a preferred embodiment, in a reaction vessel with a reflux condenser and heating apparatus, and optionally a distillation apparatus.

When the reaction product obtained from step (i) is a compound Ia, the hydrolysis is generally effected under acid conditions, as described, for example, by T. Nozoe et al., Bull. Chem. Soc. Jpn. 1989, 62, 2307. In a preferred embodiment, aqueous mineral acids are used for the hydrolysis, especially hydrochloric acid, generally in a concentration of preferably 1 to 20% by weight and more preferably 2 to 10% by weight. After the addition of the acid, the mixture is heated to a temperature of 25 to 100° C. and especially of 50 to 90° C., typically for 30 minutes to 10 hours and especially 1 to 5 hours. If the solvent has been removed after step (i), the mixture is optionally taken up beforehand in a preferably polar organic solvent. The reaction mixture obtained after the hydrolytic conversion of the compound Ia is worked up by methods known to those skilled in the art. For example, if the Ar radical is phenyl, the benzaldehyde released can first be distilled off in an azeotrope with water, and the aqueous residue, optionally after adjustment of the pH, can be extracted with an organic solvent.

When the reaction product obtained from step (i) is a compound Ib, the hydrolysis is effected either by adding an acid or a base. The basic hydrolysis can be performed, for example, in analogy to the reaction described by A. I. Meyers et al., Tetrahedron Lett. 1990, 31, 4723. For acidic hydrolysis, preference is given to using aqueous mineral acids, especially sulfuric acid, generally as a 0.5 to 5 molar and preferably as a 1 to 3 molar aqueous solution. After the addition of the acid, the mixture is heated to a temperature of 25 to 100° C. and especially of 50 to 90° C. until complete or virtually complete conversion of the compound Ib. If the solvent has been removed after step (i), the mixture is optionally taken up beforehand in a preferably polar organic solvent, for example butanol. The reaction mixture obtained after the hydrolytic conversion of the compound Ia is worked up by methods known to those skilled in the art. For example, it is possible first, if the $R^3$ and $R^4$ radicals are, for example, each methyl, to remove the hydrolysis product of the formula I by extraction with a water-insoluble organic solvent from the dimethylformamide released. In this case, it may be advantageous, especially in the case of use of water-miscible solvents in steps (i) and/or (ii), to at least partly remove the solvent before the extraction, for example by distillation.

Alternatively, in step (ii), the conversion of the amidine group of a compound Ib to the amino function can also be effected by hydrogenation, for example by means of the process described by L. Lebeau et al., J. Org. Chem. 1999, 64, 991.

The crude products of the substituted 2-aminobiphenyl I obtained after the workup of the hydrolysis of a compound Ia or Ib in step (ii) can, for further purification, be subjected to one or more processes known to those skilled in the art, for example recrystallization, distillation, sublimation, zone melting, melt crystallization or chromatography.

The invention further provides a process for preparing compounds of the formula IV

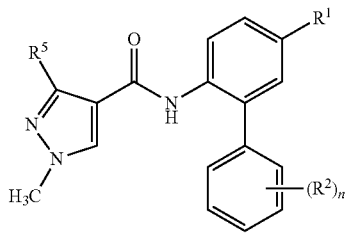

(IV)

where
n, $R^1$ and $R^2$ are each as defined above, and
$R^5$ is methyl or halomethyl,
comprising the provision of the 2-aminobiphenyl of the formula I by the process according to the invention and subsequent N-acylation of the 2-aminobiphenyl of the formula I with a compound of the formula V

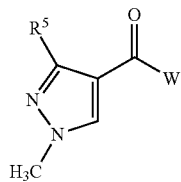

(V)

where $R^5$ is as defined above and W is a leaving group to obtain a compound of the formula IV.

With regard to suitable and preferred compounds I, reference is made completely to the statements made above.

A compound I is converted to a pyrazolecarboxamide of the formula IV by customary prior art processes for amide formation.

In general, for the inventive N-acetylation of an aminobiphenyl I, the reagent V used is a carboxylic acid or a derivative of a carboxylic acid capable of amide formation, for instance an acid halide, acid anhydride or ester. Accordingly, the leaving group W is typically hydroxyl, halide, especially chloride or bromide, an —$OR^7$ radical or an —O—CO— $R^8$ radical, where the definitions of the $R^7$ and $R^8$ substituents are explained hereinafter.

When the reagent V is used in the form of the carboxylic acid (W=OH), the reaction can be performed in the presence of a coupling reagent. Suitable coupling reagents (activators) are known to those skilled in the art and are selected, for example, from carbodiimides such as DCC (dicyclohexylcarbodiimide) and DCI (diisopropylcarbodiimide), benzotriazole derivatives such as HBTU ((O-benzotriazol-1-yl)-N,N', N'-tetramethyluronium hexafluorophosphate) and HCTU (1H-benzotriazolium-1-[bis(dimethylamino)methylene]-5-chlorotetrafluoroborate), and phosphonium activators such as BOP ((benzotriazol-1-yloxy)tris(dimethylamino)phosphonium hexafluorophosphate), Py-BOP ((benzotriazol-1-yloxy)tripyrrolidinephosphonium hexafluorophosphate) and Py-BrOP (bromotripyrrolidinephosphonium hexafluorophosphate). In general, the activator is used in excess. The benzotriazole and phosphonium coupling reagents are generally used in a basic medium.

Suitable derivatives of the carboxylic acid Y—COOH where Y is the pyrazole ring of the compound V are all derivatives which can react with the 2-aminobiphenyl I to give the amide IV, for example esters Y—C(O)—$OR^7$ (W=$OR^7$), acid halides Y—C(O)X in which X is a halogen atom (W=halogen), or acid anhydrides Y—CO—O—OC—$R^8$ (W=—O—CO—$R^8$)

The acid anhydride Y—CO—O—OC—$R^8$ is either a symmetric anhydride Y—CO—O—OC—Y ($R^8$=Y) or an asymmetric anhydride, in which —O—OC—$R^8$ is a group which can be displaced readily by the 2-aminobiphenyl I used in the reaction. Suitable acid derivatives which can form suitable mixed anhydrides with the carboxylic acid Y—COOH are, for example, the esters of chloroformic acid, e.g. isopropyl chloroformate and isobutyl chloroformate, or of chloroacetic acid.

Suitable esters Y—$COOR^7$ derive preferably from $C_1$-$C_4$-alkanols $R^7$OH in which $R^7$ is $C_1$-$C_4$-alkyl, such as methanol, ethanol, propanol, isopropanol, n-butanol, butan-2-ol, isobutanol and tert-butanol, preference being given to the methyl and ethyl esters ($R^7$=methyl or ethyl). Suitable esters may also derive from $C_2$-$C_6$-polyols, such as glycol, glycerol, trimethylolpropane, erythritol, pentaerythritol and sorbitol, preference being given to the glyceryl ester. When polyol esters are used, it is possible to use mixed esters, i.e. esters with different $R^7$ radicals.

Alternatively, the ester Y—$COOR^7$ is a so-called active ester, which is obtained in a formal sense by the reaction of the acid Y—COOH with an active ester-forming alcohol, such as p-nitrophenol, N-hydroxybenzotriazole (HOBt), N-hydroxysuccinimide or OPfp (pentafluorophenol).

Alternatively, the reagent V used for the N-acylation may possess another conventional leaving group W, for example thiophenyl or imidazolyl.

The inventive N-acylations with the above-described reagents of the formula V can be performed analogously to known processes.

Preference is given to using, for the N-acylation of compounds I, carbonyl halides V, especially those in which the leaving group W is chlorine or bromine, and is more preferably chlorine. To this end, preferably 0.5 to 4 mol and especially 1 to 2 mol of the acid chloride are used per 1 mol of the compound I.

Typically, the N-acylation of an aminobiphenyl I with an acid chloride V is performed in the presence of a base, for instance triethylamine, in which case generally 0.5 to 10 mol and especially 1 to 4 mol of the base are used per 1 mol of the acid chloride.

Frequently, a compound of the formula IV will be prepared by initially charging the corresponding compound I together with the base, preferably in a solvent, and at a temperature in the range from about –30° C. to 50° C., especially from 0° C. to 25° C., adding the acid chloride stepwise, optionally dissolved in a solvent. Typically, the reaction is subsequently allowed to continue at elevated temperature, for instance in the range from 0° C. to 150° C., especially from 15° C. to 80° C.

The acylation can, however, also be performed in the absence of a base. To this end, the acylation is performed in a biphasic system. One of these phases is aqueous, and the second phase is based on at least one essentially water-immiscible organic solvent. Suitable aqueous solvents and suitable essentially water-immiscible organic solvents are described in WO 03/37868. This reference also describes, in general terms, further suitable reaction conditions for acylation processes in the absence of bases.

The workup of the reaction mixtures obtained in the reactions for the inventive N-acylation and the isolation of the compound of the formula IV are effected in a customary manner, for example by an aqueous extractive workup, by removing the solvent, for example under reduced pressure, or by a combination of these measures. Further purification can be effected, for example, by crystallization, distillation or chromatography.

The processes according to the invention firstly allow the 2-aminobiphenyls I to be obtained with a low level of complexity, in good to very good yields and with high selectivities, and the carboxamides IV derived therefrom are secondly obtainable readily and generally quantitatively.

EXAMPLES

A. Preparation of the Zinc Organyl Compounds of the Formula III and of the Analogous Grignard Compounds The examples which follow are intended to show, by way of example, how the zinc organyl compounds and the analogous magnesium organyl compounds (Grignard compounds) used in the processes according to the invention are prepared.

A.1 3,4,5-Trifluorophenylmagnesium bromide

A nitrogen- or argon-inertized reactor was initially charged with magnesium turnings (83.2 g; 3.42 mol) and then dry, unstabilized tetrahydrofuran (THF, 1646.2 g) was added. 3,4,5-Trifluorobromobenzene (30 g; 0.14 mol) was added dropwise with stirring to this suspension at a temperature of 25° C., and the startup of the reaction was awaited, which was noticeable by a spontaneous temperature increase to approx. 32° C. Subsequently, further 3,4,5-trifluorobromobenzene (571.9 g; 2.71 mol) was metered in at a temperature of 25 to 35° C. within 5 h. To complete the reaction, stirring was continued at 25 to 30° C. for 2 h. Thereafter, the reaction mixture was filtered, the excess magnesium filtered off was washed with a little THF, and the wash solution was combined with the filtrate. The 3,4,5-trifluorophenylmagnesium bromide content of a solution in THF thus prepared was calculated, assuming full conversion of the 3,4,5-trifluorobromobenzene used, to be a 1.1 to 1.2 mmol/g solution.

A.2 3,4,5-Trifluorophenylzinc bromide

An about 1 M solution of 3,4,5-trifluorophenylzinc bromide in THF was obtained by means of a reaction analogous to the preparation of the 3,4,5-trifluorophenyl-magnesium bromide, in which the magnesium turnings were replaced by Rieke zinc.

B Preparation of the N-Derivatized 2-Aniline Compounds of the Formulae IIa and IIb The examples which follow are intended to show, by way of example, how the imine or amidine derivatives of the aniline compound II used in the process according to the invention are prepared.

B.1 Preparation of 1-phenylmethylideneamino-2-chlorobenzene

98% 2-chloroaniline (781 g; 6 mol) and 98% benzaldehyde (659.6 g; 6 mol) were dissolved in ethanol (832 g), and the solution was boiled under reflux for 8 h (heating apparatus adjusted to 90° C.). Subsequently, the reaction solution was concentrated on a rotary evaporator at 85° C. and 20 mbar and then fractionally distilled through a distillation apparatus. The main fraction distilled over at 142° C. and 1.3 mbar. 1048 g of the product were obtained in 99% purity.

EI-MS [m/z]: 215 [M]$^+$;
$^1$H NMR (500 MHz, CDCl$_3$): δ=7.0 (d, 1H); 7.1 (t, 1H); 7.23 (dd, 1H); 7.4 (d, 1H); 7.45-7.5 (m, 3H); 7.93 (d, 2H); 8.34 (s, 1H) ppm;
$^{13}$C NMR (125 MHz, CDCl$_3$): δ=118.9; 126.3. 127.8; 128.8; 129.1; 129.4; 130.1; 131.8; 35.9; 149.6; 162.1 ppm.

B.2 Preparation of N,N-dimethyl-N'-(2-chlorophenyl)formamidine

98% 2-chloroaniline (195 g; 1.5 mol) and 98% dimethylformamide dimethyl acetal (228.2 g; 1.8 mol) were dissolved in toluene (300 g), and the solution was heated under reflux for 4 h. During this time, the internal temperature fell from 96 to 77° C. Thereafter, 15 g of distillate were removed, and the internal temperature rose again during this time to 84° C. Finally, the reaction solution was concentrated on a rotary evaporator at 90° C. and 5 mbar and the resulting brown oil (270.5 g) was fractionated by means of column distillation. The main fraction distilled over at 120° C. and 1.4 mbar and comprised the product in a purity of >99% (determined using area percentages of the GC spectrum).

EI-MS [m/z]: 182 [M]$^+$;
$^1$H NMR (500 MHz, DMSO): δ=2.9 (s, 6H); 6.85-6.95 (m, 2H); 7.1-7.16 (m, 1H); 7.34 (d, 1H); 7.58 (s, 1H) ppm;
$^{13}$C NMR (125 MHz, CDCl$_3$): δ=33.9; 120.8; 122.5; 127.2; 127.4; 129.4; 149.1; 153.6 ppm.

C Preparation of Ring-Substituted 2-Aminobiphenyls of the Formula I from Aniline Compounds of the Formula II with a Free Amino Group The examples which follow are intended to show, by way of example, how the substituted 2-aminobiphenyls of the formula I are prepared proceeding from the 2-haloanilines of the formula II by means of the process according to the invention. In both examples, the zinc organyl is obtained in situ from the corresponding Grignard compound.

C.1 Preparation of 3,4,5-trifluoro-2'-aminobiphenyl from 2-bromoaniline

A 100 ml glass flask was initially charged with zinc chloride (4.8 mmol) dissolved in toluene (0.5 M solution), and a solution of 3,4,5-trifluorophenylmagnesium bromide (4.5 mmol; 1.15 mmol per g of solution) in THF was added thereto at a temperature of 25° C. After stirring for 20 min, N-methylpyrrolidone (6.8 g) was added to the reaction solution. A further 5 min later, tri-tert-butylphosphonium tetrafluoroborate (18.2 mg), bis(dibenzylideneacetone)palladium(0) (18.2 mg) and 2-bromoaniline (0.54 g; 3 mmol) were added. The reaction solution was subsequently stirred at a temperature of 25° C. for 5 h. Thereafter, the reaction mixture was added to 10% by weight hydrochloric acid and, after the pH had been adjusted to 12 with sodium chloride solution, the mixture was extracted with diethyl ether.

Gas chromatography analysis of the organic phase showed that the main product, 3,4,5-trifluoro-2'-aminobiphenyl, relative to the 2-bromoaniline reactant and the 1,2,3-trifluorobenzene and 3,4,5,3',4',5'-hexafluorobiphenyl by-products, was present in a ratio of 44:3:39:3. Assuming that the Grignard compound used had formed only the main product and the two abovementioned by-products, this gives rise to a yield of 55% based on the 2-bromoaniline.

C.2 Preparation of 3,4,5-trifluoro-2'-aminobiphenyl from 2-chloroaniline

In a 100 ml glass flask, a solution of 3,4,5-trifluorophenylmagnesium bromide (4.5 mmol; 1.15 mmol per g of solution) in THF was added to solid zinc chloride (0.9 g; 6.4 mmol) at a temperature of 25° C. After stirring for 30 min, 12.7 ml of N-methylpyrrolidone were added to the reaction solution. A further 15 min later, (1,3-bis-(2,6-diisopropylphenyl)imidazol-2-ylidene)(3-chloropyridyl)palladium(II)dichloride (27 mg) and, after a further 15 min, 2-chloroaniline (0.51 g; 4 mmol) were added. The reaction solution thus obtained was stirred at a temperature of 25° C. for 2 h and then heated under reflux for 4 h. Thereafter, a weighed sample of the reaction mixture was hydrolyzed in a volumetric flask with 1 ml of 10% hydrochloric acid, and was made up to the mark with acetonitrile and water. The analysis of the standard solution thus obtained, performed by quantitative HPLC, showed that the reaction mixture comprised 2.6 mmol of 3,4,5-trifluoro-2'-aminobiphenyl. This corresponds to a yield of 65% based on 2-chloroaniline.

D Preparation of N-Derivatized 2-Aminobiphenyls of the Formulae Ia and Ib from Aniline Derivatives of the Formulae IIa and IIb and Subsequent Hydrolysis to the 2-Aminobiphenyls with a Free Amino Group The examples which follow are intended to show, by way of example, how the N-derivatized 2-aminobiphenyls of the formulae Ia and Ib are prepared proceeding from the N-derivatized 2-haloanilines of the formulae IIa and IIb by means of the process according to the invention, and then optionally, converted hydrolytically to the corresponding 2-aminobiphenyls of the formula I.

D.1 Preparation of 2-phenylmethylideneamino-3',4', 5'-trifluorobiphenyl from phenylmethylideneamino-2-chlorobenzene In a 750 ml reactor, a mixture of zinc chloride (20 g; 0.147 mol) and THF (76 g) was heated to a temperature of 30° C. Subsequently, a solution of 3,4,5-trifluorophenyl-magnesium bromide (0.133 mol) in THF (1.15 mmol per g of solution) was added. After stirring for 10 minutes, (1,3-bis(2,6-diisopropylphenyl)imidazol-2-ylidene)(3-chloro-pyridyl)palladium(II)dichloride (462 mg) was added at a temperature of 25° C. A further 5 min later, N-methylpyrrolidone (30 g) was added to the reaction mixture, and, after a further 10 min, 99% phenylmethylideneamino-2-chlorobenzene (29 g; 0.133 mol). Thereafter, the mixture was heated to 50° C. and stirred at this temperature for 6 h. For workup, water (300 g), conc. hydrochloric acid (22 g) and diethyl ether (300 g) were added and mixed in a separating funnel. Subsequently, the organic phase was removed and the aqueous phase was extracted once more with diethyl ether (300 g). The combined organic phases were concentrated by evaporation on a rotary evaporator to give a dark oil which rapidly crystallized through (81.3 g). Gas chromatography analysis showed that two products were present in a ratio of 81:19, which were the imine derivative, 2-phenylmethylideneamino-3',4',5'-trifluorobiphenyl, and the hydrolysis product formed therefrom, 3,4,5-trifluoro-2'-aminobiphenyl. The identity of the more intense signals in the GC analysis was confirmed by independent synthesis of the imine derivative from 3,4,5-trifluoro-2'-aminobiphenyl and benzaldehyde.

Since the imine derivative was hydrolyzed completely to 3,4,5-trifluoro-2'-aminobiphenyl under the conditions of the quantitative HPLC analysis, the overall yield of biphenyl coupling product corresponded to the value of 123 mmol determined for 3,4,5-trifluoro-2'-aminobiphenyl by quantitative HPLC. This corresponds to a yield of 92% based on the phenylmethylideneamino-2-chlorobenzene used.

EI-MS [m/z]: 311 [M]$^+$;

$^1$H NMR (500 MHz, CDCl$_3$): δ=7.05 (d, 1H); 7.1-7.2 (m, 2H); 7.25-7.3 (m, 1); 7.32-7.5 (m, 5H); 7.76-7.82 (d, 2H); 8.45 (s, 1H) ppm;

$^{13}$C NMR (125 MHz, CDCl$_3$): δ=114.25; 118.95; 126.36; 128.90; 128.94; 129.54; 129.88; 131.66; 132.62; 135.65; 136.14; 138.89; 149.49; 150.62; 160.64 ppm.

D.2 Preparation of 3,4,5-trifluoro-2'-aminobiphenyl from phenylmethylideneamino-2-chlorobenzene In a 1 l reactor, a mixture of zinc chloride (20 g; 0.147 mol) and THF (29 g) was heated to a temperature of 30° C. Subsequently, a solution of 3,4,5-trifluorophenylmagnesium bromide (0.133 mol) in THF (1.15 mmol per g of solution) was added. After stirring for 10 minutes, (1,3-bis(2,6-diisopropylphenyl)imidazol-2-ylidene)(3-chloropyridyl)-palladium(II) dichloride (462 mg) was added at a temperature of 25° C. A further 5 min later, N-methylpyrrolidone (30 g) was added to the reaction mixture and, after a further 10 min, 99% phenylmethylideneamino-2-chlorobenzene (29 g; 0.133 mol). Thereafter, the mixture was heated to 50° C. and stirred at this temperature for 6 h. For workup, 3.4 g of activated carbon were added, and the resulting suspension was stirred for 1 h and then filtered through kieselguhr. The filter cake was rinsed with THF (200 g) and then the filtrate was concentrated on a rotary evaporator at a temperature of 50° C. in a vacuum of down to 5 mbar. Water (200 g) and conc. sulfuric acid (28 g) were added to the remaining residue. The mixture was stirred at a temperature of 80° C. for 3 h and the benzaldehyde released was distilled off in an azeotrope with water. Subsequently, sodium hydroxide solution was used to establish a pH of 2.8, and toluene (200 g) was added. After the phase separation, the aqueous phase was extracted once more with toluene (200 g), and the combined organic phases were washed with water (100 g) and concentrated on a rotary evaporator at 80° C. and 5 mbar to give a dark oil (26.7 g), which crystallized when left to stand.

Analysis by quantitative HPLC showed that 86.4% by weight of the oil formed was accounted for by 3,4,5-trifluoro-2'-aminobiphenyl, which corresponds to a yield of 78%.

D.3 Preparation of N,N-dimethyl-N'-(3',4',5'-trifluorobiphenyl-2-yl)formamidine and hydrolysis to 3,4,5-trifluoro-2'-aminobiphenyl A 1 l reactor was initially charged with a solution (132.2 g; 1 M) of 3,4,5-trifluorophenyl-zinc bromide in THF and diluted with THF (104.9 g). Thereafter, (1,3-bis(2,6-diisopropylphenyl)imidazol-2-ylidene)(3-chloropyridyl)palladium (II)dichloride (461.8 mg) were added at a temperature of 25° C. A further 5 min later, N-methylpyrrolidone (29.9 g) and, after a further 10 min, N,N-dimethyl-N'-(2-chlorophenyl)formamidine (24.4 g; 0.133 mol) were added to the mixture. Thereafter, the mixture was heated to 50° C. and stirred at this temperature for 6 h. After being left to stand overnight at a temperature of 25° C., the mixture was heated to reflux for another 1 h and cooled again to 25° C. For workup, 2.5 g of activated carbon were added, and the mixture was stirred overnight and filtered through kieselguhr. The filter cake was washed with a further 200 g of THF.

The proportion of the N,N-dimethyl-N'-(3',4',5'-trifluorobiphenyl-2-yl)formamidine product in the combined filtrate (387.8 g) was, according to analysis by means of quantitative HPLC, 8.4% by weight, which corresponds to a yield of 89%.

The identity of the N,N-dimethyl-N'-(3',4',5'-trifluorobiphenyl-2-yl)formamidine present in the filtrate was confirmed by independent synthesis from 3,4,5-trifluoro-2'-aminobiphenyl and dimethoxymethyldimethylamine.

EI-MS [m/z]: 278 [M]$^+$;

$^1$H NMR (500 MHz, CDCl$_3$): δ=2.88 (s, 3H); 3.0 (s, 3H); 6.95 (d, 1H); 7.02 (t, 1H); 7.2-7.3 (m, 2H); 7.4-7.5 (m, 2H); 7.6 (s, 1H) ppm;

$^{13}$C NMR (125 MHz, CDCl$_3$): δ=33.71; 39.21; 114.01; 114.25; 119.67; 122.15; 129.87; 130.65; 137.17; 137.41; 149.62; 149.27; 153.04.

For hydrolytic conversion, the crude product was dissolved in n-butanol and, after addition of aqueous sulfuric acid (2 M), heated under reflux. The 3,4,5-trifluoro-2'-aminobiphenyl product was obtained as a solution in n-butanol.

The invention claimed is:

1. A process for preparing a compound of formula (I)

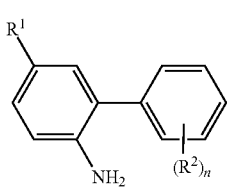

(I)

in which
n is 0, 1, 2 or 3,
R$^1$ is hydrogen, cyano or fluorine, and
each R$^2$ is independently selected from cyano, fluorine, C$_1$-C$_4$-alkyl, C$_1$-C$_4$-fluoroalkyl,
C$_1$-C$_4$-alkoxy, C$_1$-C$_4$-fluoroalkoxy, C$_1$-C$_4$-alkylthio and C$_1$-C$_4$-fluoroalkylthio, comprising:

(i) reacting a compound of formula (II) with a compound of formula (III)

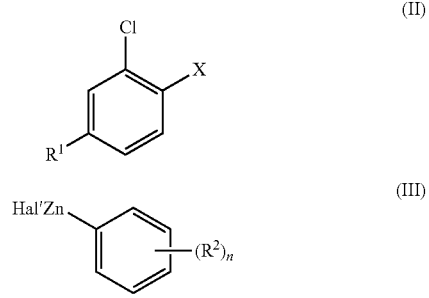

in which
Hal' is bromine or chlorine, and
X is NH$_2$ or an X$^1$ or X$^2$ radical
X$^1$:

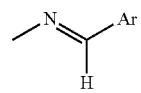

X$^2$:

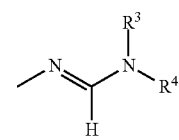

in which
Ar is phenyl which optionally bears 1, 2 or 3 substituents which are selected from the group consisting of C$_1$-C$_4$-alkyl and C$_1$-C$_4$-alkoxy, and
R$^3$ and R$^4$ are each independently C$_1$-C$_6$-alkyl,
in the presence of a palladium catalyst comprising palladium and one or more complex ligands,
and, when X in formula II is an X$^1$ or X$^2$ radical,
(ii) converting the product obtained in step (i) to the compound of formula (I).

2. The process according to claim 1, wherein X is an X$^1$ or X$^2$ radical.

3. The process according to claim 1, wherein R$^1$ is hydrogen or fluorine, R$^2$ is fluorine and n is 2 or 3.

4. The process according to claim 1, wherein Hal' is chlorine.

5. The process according to claim 1, wherein step (i) is performed in an organic solvent in which an ether is present.

6. The process according to claim 5, wherein the organic solvent is a mixture of an ether and N-methylpyrrolidone.

7. The process according to claim 1, wherein the compound of formula (III) is generated in situ from the corresponding Grignard compound.

8. The process according to claim 1, wherein palladium is palladium in the 0 or 2 oxidation state.

9. The process according to claim 1, wherein the complex ligand comprises monodentate phosphine of formula (VI) and/or bidentate phosphine of formula (VII):

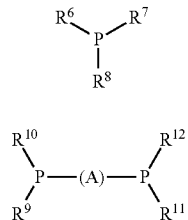

in which $R^6$, $R^7$, $R^8$, $R^9$, $R^{10}$, $R^{11}$ and $R^{12}$ are each independently $C_1$-$C_8$-alkyl, $C_5$-$C_8$-cycloalkyl, adamantyl, aryl-$C_1$-$C_2$-alkyl, ferrocenyl or aryl which is optionally substituted by $C_1$-$C_4$-alkyl, $C_1$-$C_4$-alkoxy, fluorine or chlorine; and A is ferrocenediyl or a linear $C_2$-$C_5$-alkanediyl which is optionally substituted by $C_1$-$C_8$-alkyl or $C_3$-$C_6$-cycloalkyl and is optionally part of one or two mono- or bicyclic rings which are unsubstituted or substituted.

10. The process according to claim 1, wherein the complex ligand comprises at least one imidazolylidene compound of the formula IX:

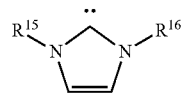

in which $R^{15}$ and $R^{16}$ are each independently aryl or hetaryl, where aryl and hetaryl are each unsubstituted or bear 1, 2, 3 or 4 substituents selected from $C_1$-$C_8$-alkyl and $C_3$-$C_7$-cycloalkyl.

11. A process for preparing pyrazolecarboxamides of the formula IV

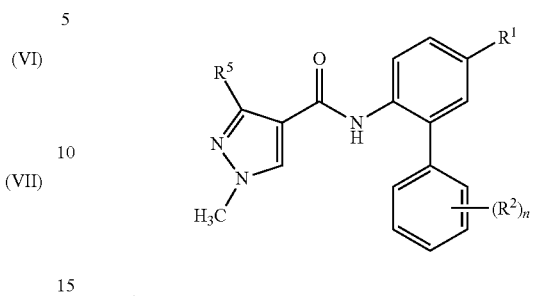

where
n is 0, 1, 2 or 3,
$R^1$ is hydrogen, cyano or fluorine, and
each $R^2$ is independently selected from cyano, fluorine, $C_1$-$C_4$-alkyl, $C_1$-$C_4$-fluoroalkyl, $C_1$-$C_4$-alkoxy, $C_1$-$C_4$-fluoroalkoxy, $C_1$-$C_4$-alkylthio and $C_1$-$C_4$-fluoroalkylthio, and
$R^5$ is methyl or halomethyl,
comprising N-acylating the compound formula (I) prepared according to claim 1 with a compound of the formula (V)

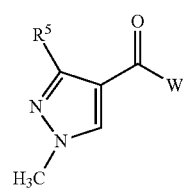

wherein W is a leaving group
to obtain the compound of the formula (IV).

12. The process according to claim 11, wherein W is hydroxyl or halogen.

* * * * *